United States Patent

Wood

Patent Number: 5,533,506
Date of Patent: Jul. 9, 1996

[54] NASAL TUBE ASSEMBLY

[75] Inventor: Thomas J. Wood, Blackshear, Ga.

[73] Assignee: Medlife, Inc., Charlotte, N.C.

[21] Appl. No.: 372,227

[22] Filed: Jan. 13, 1995

[51] Int. Cl.$^6$ .......... A61M 15/08; A61M 16/00; A61M 11/00; A62B 7/00

[52] U.S. Cl. .............. 128/207.18; 128/200.26; 128/DIG. 26; 128/912; 604/94; 604/178

[58] Field of Search .............. 128/207.18, 203.26, 128/204.12, 205.13, 206.11, 206.18, 207.13, DIG. 26, 912; 604/94, 178, 179

[56] References Cited

U.S. PATENT DOCUMENTS

| | | | |
|---|---|---|---|
| D. 333,015 | 2/1993 | Farmer et al. | D19/8 |
| 853,431 | 5/1907 | Allen | 128/207.18 |
| 2,057,397 | 10/1936 | Strauch | 128/206.11 |
| 2,672,138 | 3/1954 | Carlock | 128/207.18 |
| 2,693,182 | 11/1954 | Phillips | 128/207.14 |
| 3,902,486 | 9/1975 | Guichard | 128/140 |
| 4,106,505 | 8/1978 | Salter et al. | 604/94 |
| 4,114,626 | 9/1978 | Beran | 604/178 |
| 4,248,229 | 2/1981 | Miller | 604/179 |
| 4,270,529 | 6/1981 | Muto | 128/200.26 |
| 4,736,741 | 4/1988 | Payton et al. | 128/207.18 |
| 4,793,343 | 12/1988 | Cummins, Jr. et al. | 128/204 |
| 4,840,169 | 6/1989 | Folsom | 128/863 |
| 4,850,346 | 7/1989 | Michel et al. | 128/206 |
| 4,967,742 | 11/1990 | Theodorou | 128/202 |
| 5,011,474 | 4/1991 | Brennan | 604/54 |
| 5,074,297 | 12/1991 | Venegas | 128/204 |
| 5,121,745 | 6/1992 | Israel | 128/202 |
| 5,127,397 | 7/1992 | Kohnke | 128/202 |
| 5,265,592 | 11/1993 | Beaussant | 128/201 |
| 5,265,595 | 11/1993 | Rudolph | 128/204 |
| 5,372,130 | 12/1994 | Stern et al. | 128/205 |

FOREIGN PATENT DOCUMENTS 532214   1/1941   United Kingdom ............ 604/94

*Primary Examiner*—Kimberly L. Asher
*Assistant Examiner*—Virendra Srivastava
*Attorney, Agent, or Firm*—Bernstein & Associates

[57] ABSTRACT

A nasal ventilation system comprising a tube terminating in a pair of nasal inserts. Each insert tapers at its end and has a soft membrane covering the tapered end for wearer comfort. A washer positioned below the membrane provides a positive seal with the nostril and prevents gas leakage by resting on the support bar. A support bar having slots which can accommodate the nasal inserts also permits lateral movement of the inserts for positioning of the inserts within the nostrils. An adjustable harness system is removably secured to the wearer.

5 Claims, 2 Drawing Sheets

NASAL TUBE ASSEMBLY

FIELD OF THE INVENTION

The present invention relates to nasal ventilation systems, and more particularly to a nasal ventilation insert.

BACKGROUND OF THE ART

Nasal ventilators consist of tubes and other means for delivering gases adapted for use with the nasal or oral passage of a patient. Typically, a nasal ventilator system comprises a gas source, such as a volume ventilator, CPAP system, PIPAP, or IPPB. The gas is most often room air, but can be a mixture of gases. The gas is transported by a thin flexible tube made of an inert material. In a low flow oxygen system, the tube terminates in an opening which can be inserted into the nostril. Typically, the tube splits at a Y-junction into two smaller tubes or a pair of smaller tubes protrude from tube, each smaller tube carrying gas to one nostril via a nasal cannula, thereby increasing the fraction of inspired oxygen.

Conventional nasal ventilation systems use a mask which fits over the nose to deliver a supply of oxygen to the patient. Such systems frequently suffer from air leaking out around the mask, creating an inability to assure ventilation in many patients. Such systems are usually very position dependent, whereby if the mask is moved slightly with respect to the facial contour or with respect to the nose, leakage occurs. As a result many patients lose interest in using the nasal mask. Additionally, with such system, the mask can become uncomfortable when not in position, thus requiring the patient to remain rather still in order to alleviate the discomfort and to maintain oxygen inspiration.

It is important that as much of the gas being transported by the tube reach the lungs of the patient. Conventional tube delivery systems suffer from the disadvantage of not providing a positive seal between the tube and the nostril, resulting in gas leakage around the nasal mask, .which escapes around the mask. It would be desirable for a nasal cannula to form a positive seal within the nostril to pass as much gas as desired to the patient,

SUMMARY OF THE INVENTION

The present invention provides a nasal ventilation system having a nasal insert that is inserted into the nostril and is comprises an insert tube and a soft membrane covering the tube. A washer assists the membrane in forming a positive seal between the nasal insert and the nostril to prevent escape of gas. A mask has a support bar comprising a pair of slots that can accommodate the nasal insert tubes in order to properly position them beneath and/or within the nostrils.

A harness supports the support bar and the nasal inserts and is removably attachable to the patient.

Accordingly, it is an object of the present invention to provide a nasal ventilation system having improved comfort for use over extended periods.

It is another object of the present invention to provide a nasal ventilation system having increased gas delivery efficiency and with no leakage of gas from the nostrils.

It is a further object of the present invention to provide a nasal ventilation system having a nasal insert having a soft membrane which is in contact with the nostril.

It is still another object of the present invention to provide a nasal ventilation system having an adjustable support system for use by patients with different anatomical structures.

It is still another object of the present invention to provide a nasal ventilation system having a rubber washer to provide a means for supporting the nasal inserts in the nostrils.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures of which.

DESCRIPTION OF THE PREFERRED EMBODIMENTS

Figure 1:
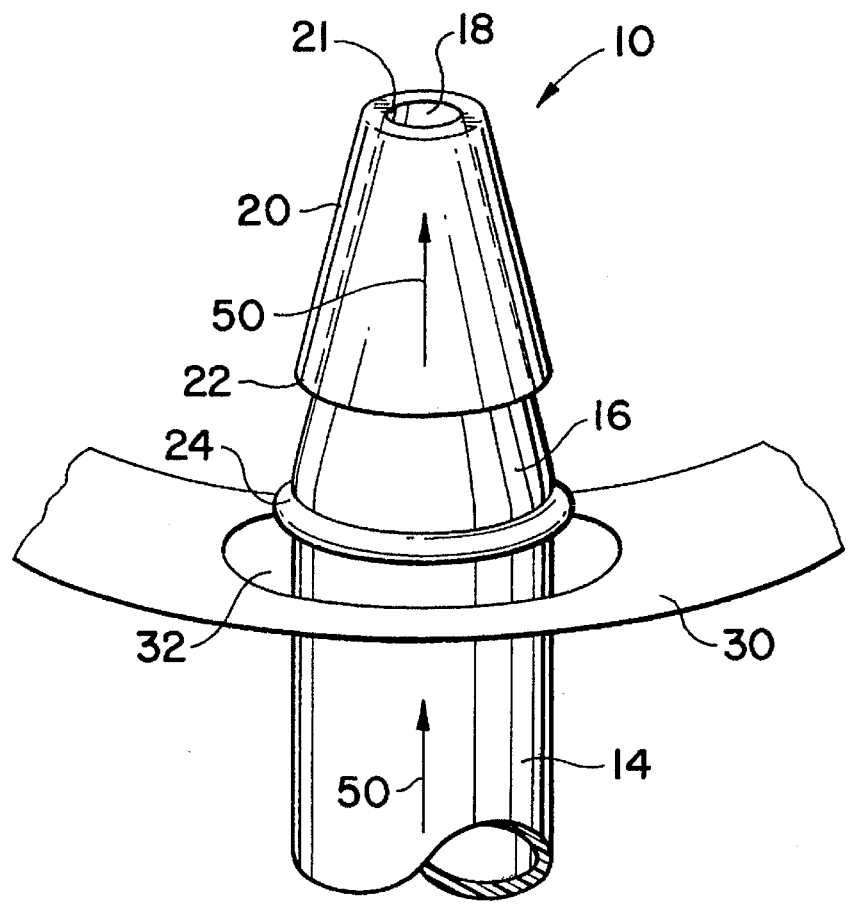
FIG. 1 shows a perspective view of a nasal insert of the present invention.

FIG. 1 shows a nasal insert system 10 comprising a hollow tube 14 having a tapered end 16 terminating in an aperture 18. The tube 14 can be made of any conventional material, such as polymer plastic or surgical rubber. It is desirable for the tube to be flexible and biologically inert.

An outer membrane 20 comprises a conical segment of relatively soft, flexible, biologically inert material that has a top end 21 and a bottom end 22. The outer membrane 20 has an overall diameter that is generally similar to that of the tapered end 16 of the tube 14, thus permitting an airtight seal between outer membrane and the tapered end 16 when the outer membrane 20 is fitted over the tapered end 16. The outer membrane 20 will be in contact with the nasal passages and should be made of a soft material to provide comfort to a user. Such materials are known in the art, such as, but not limited to inflated rubber membranes, such as that material used for ear plugs that expend with heat at 37° C.

The portion of the insert 10 which provides the seal in the nostrils is preferably one-half inches long and one-half inches in width, with a slightly taper toward the opening 18.

A washer 24, made of rubber, plastic or the like, is seated concentrically around the outer wall of the tube 14 below the outer membrane 20. The washer 24 prevents the nasal inserts 10 from falling through the openings in the support bar, as described in detail below.

A support bar 30 is a relatively thin piece of plastic, metal, ceramic, composite, impregnated fabric, rubber, or the like. The bar 30 has at least two slots 32 and 34 defined therein that are large enough in diameter as to accommodate a nasal insert 10. One feeds the tube through the slot and then places the gasket and membrane over the end. The slot 32 permits lateral movement of the tube 14 within the slot 32 so that the insert 10 can be positioned for use with a particular patient's anatomy. Once in place the inserts 10 are restricted from substantial lateral movement by being firmly supported within the nostrils.

The nasal insert 10 of the present invention can be used in conjunction with a harness 40 which supports and maintains the insert 10 in a relatively fixed and comfortable position within the nostril. It is to be understood that a number of harness configurations can be used. The present invention provides for a novel harness configuration that provides improved comfort and efficiency in maintaining the nasal inserts 10 in the nostrils in comfort.

In its most basic form, the harness 40 comprises a shell 42, which is formed preferably as a single piece of plastic or padded bendable material which has the general shape of the nasal area of the face (or can conform to the patient's shape) about one to one and one-half inches on the sides of the nose. The shell 42 is padded underneath with a material 43 (not shown) that preferably is easily compressible and optionally can expand when exposed to body temperature and conform generally to the nose and facial contours. The padding 43 is preferably coated with a non-absorbent coating to prevent absorption of body fluids.

The inserts 10 are connected to the shell 42 by a pair of loops 44 on the support bar 30. Both tubes 14 are connected at a junction 44 to an attachment piece 46. The attachment piece 46 can be connected directly, or by an adapter 48 (not shown) to a volume ventilator, BIPAP machine, CPAP machine or IPPB machine. The attachment piece 46 can swivel freely thus allowing the ventilator to be placed on either side of, above or behind the patient. The seal at the attachment piece 46 is air tight.

A set of support straps 50 are connected to the peripheral areas of the shell 42. The straps 50 are connected to a connector 52 which is a C-shaped piece of material, preferably plastic, which affords user comfort. The connector 52 can be padded to eliminate irritation from rubbing against the skin. The connector 52 is connected to a the first end 54 of a strap 56 which wraps around the ear. The strap 56 is made of a soft, flexible material, such as fabric or leather, which will provide user comfort during extended use. The second end 57 of the strap 56 is connected by a bridge connector 58 to the shell 40. Optionally, a secondary support strap 59 can be connected between the shell 40 and the support strap 50.

It is preferable that the support harness 40 be thin, comfortable, adjustable, and be part or all elastic.

In use the insert 10 is fed through the slot 32 in the support bar 30. The washer 24 is placed over the insert 10 to prevent the tube 14 from sliding back out of thé slot 32. The insert 10 is placed in the appropriate nostril and seated with the outer membrane 20 being in contact with the nostril. The straps 56 of the harness 40 are adjusted until snug but comfortable. The harness then is connected by the attachment piece 46 to a gas tube. After the gas tube is attached, the ventilation source is turned on and the patient can comfortably breathe yet maintain full head movement and substantially a full field of view. Arrow 50 shows the direction of the flow of air through the tube 14.

Figure 2:
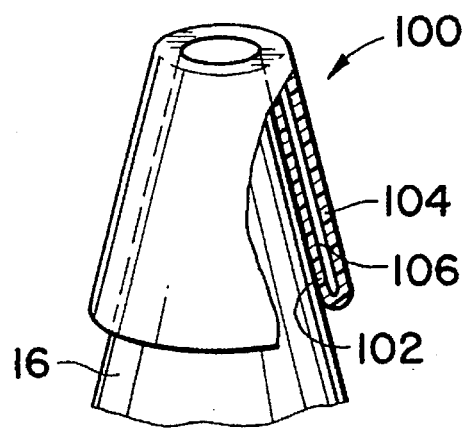
FIG. 2 shows an alternative embodiment of the outer membrane.
Figure 3:
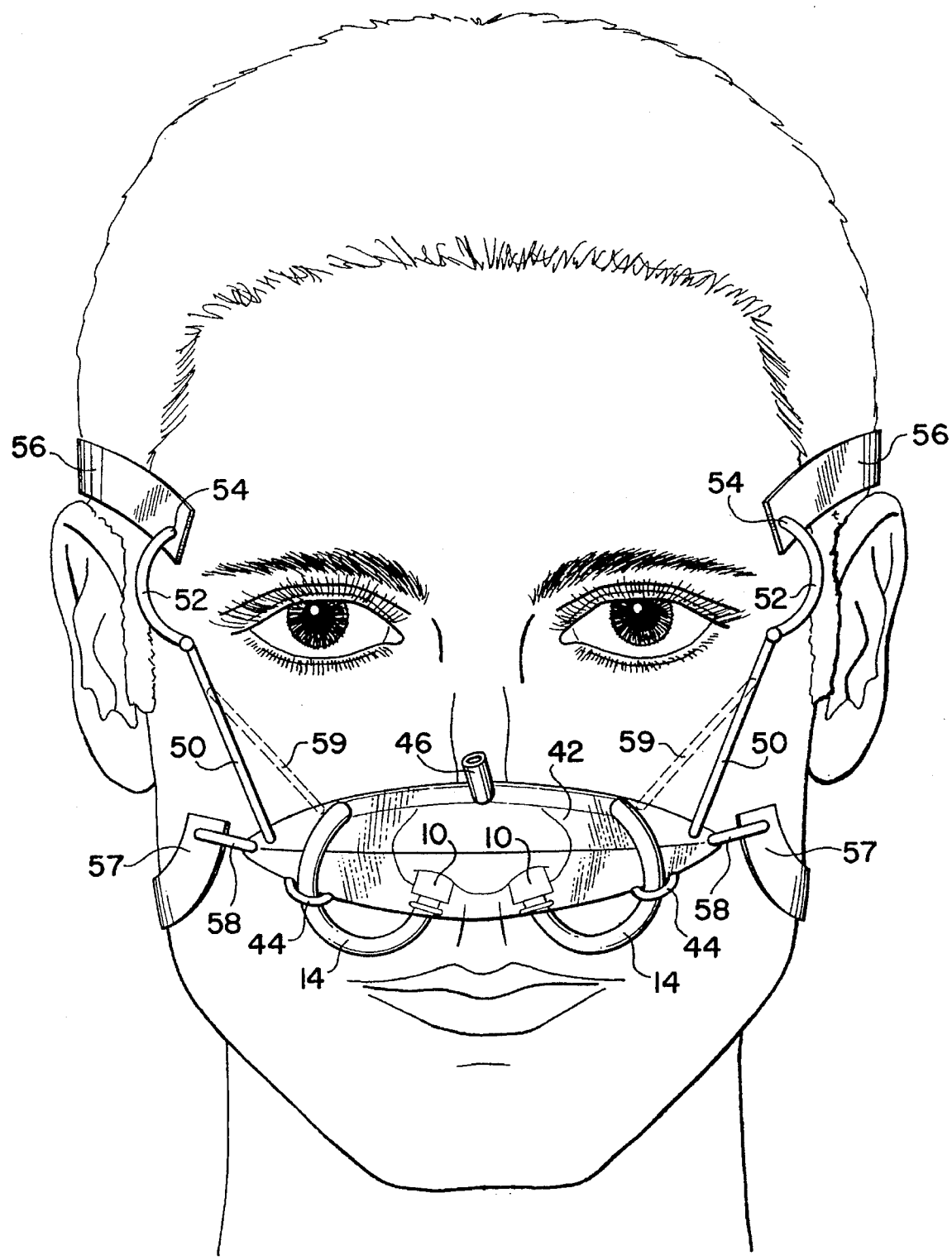
FIG. 3 shows a perspective view of the nasal insert mounted in a shell and strapped to a patient.

In an alternative embodiment, shown in FIG. 2, a membrane 100 can be a made of an inner wall 102 and an outer wall 104. The inner wall 102 and the outer wall 104 can be sealed, thereby providing a space 106 which can contain air. This embodiment provides an air cushioned nasal insert outer membrane which, when inserted into the nostril, will form a positive seal by compressing slightly against the inside of the nasal passage.

An advantage of the insert of the present invention is that the soft outer membrane 20 permits extended use of a ventilation system without causing irritation of the nasal passages. Since the outer membrane 20 is replaceable, it will not be a meaningful source of infection. The washer 24 provides a positive seal in the nostrils to prevent escape of gas from the tube aperture 18 out of the nose before first being inhaled by resting on top of the support bar 30.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

I claim:

1. A nasal tube assembly comprising:

a tube tapered at one end and having an aperture defined at said tapered end;

a means removably associated with said tapered end for forming a seal when said tapered end is inserted into a nostril;

a support bar which comprises a generally flat strip of material having at least one slot defined therein, said slot having a width, said tube being slidable within said slot and having a degree of lateral movement therein due to the width of said slot; and a means for preventing said tube from easily slipping through said slot comprising a washer sized to have a diameter larger than the width of said slot, said washer snugly engaging said tube, and being positioned between said tapered end of said tube and said support bar.

2. The nasal tube assembly of claim 1, wherein said seal :forming means comprises a conical shaped membrane capable of being removably associated with said tapered end.

3. The nasal tube assembly of claim 1, wherein said seal forming means is made of a soft, flexible material.

4. The nasal tube assembly of claim 2, wherein said seal forming means is made of a foam material.

5. The nasal tube assembly of claim 1 further comprising a harness removably attachable to a patient, said harness being attached to said support bar.

\* \* \* \* \*